US012807551B2

(12) United States Patent
Matsuda et al.

(10) Patent No.: US 12,807,551 B2
(45) Date of Patent: Nov. 24, 2026

(54) METHOD FOR PRODUCING METHANOL

(71) Applicant: Sumitomo Chemical Company, Limited, Tokyo (JP)

(72) Inventors: Masato Matsuda, Niihama (JP); Tetsuya Suzuta, Niihama (JP); Takehiro Nakasuji, Niihama (JP); Yuichi Sato, Niihama (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 731 days.

(21) Appl. No.: 18/022,831

(22) PCT Filed: Aug. 30, 2021

(86) PCT No.: PCT/JP2021/031683
§ 371 (c)(1),
(2) Date: Feb. 23, 2023

(87) PCT Pub. No.: WO2022/045328
PCT Pub. Date: Mar. 3, 2022

(65) Prior Publication Data

US 2023/0312444 A1 Oct. 5, 2023

(30) Foreign Application Priority Data

Aug. 31, 2020 (JP) ................................ 2020-145859

(51) Int. Cl.
*C07C 29/152* (2006.01)
*B01J 8/02* (2006.01)
(Continued)

(52) U.S. Cl.
CPC ........... *C07C 29/152* (2013.01); *B01J 8/0285* (2013.01); *C07C 29/151* (2013.01); *C07C 29/1518* (2013.01); *C10J 3/00* (2013.01)

(58) Field of Classification Search
None
See application file for complete search history.

(56) References Cited

U.S. PATENT DOCUMENTS 5,104,419 A 4/1992 Funk
2010/0312021 A1* 12/2010 Thorhauge ............ B01J 8/0292
422/201
(Continued)

FOREIGN PATENT DOCUMENTS

JP 2005125244 A 5/2005
JP 2005298413 A 10/2005
(Continued)

OTHER PUBLICATIONS

Machine translation of JP2011143370A, Jul. 28, 2011, pp. 1-51 (Year: 2011).*

(Continued)

*Primary Examiner* — Medhanit W Bahta
(74) *Attorney, Agent, or Firm* — Panitch Schwarze Belisario & Nadel LLP

(57) ABSTRACT

This method includes a gas acquisition step (S1) of obtaining a gas containing a carbon oxide and hydrogen from a waste material from which methanol is to be produced and a conversion step (S6) of bringing at least a portion of the gas into contact with a catalyst to convert the portion of the gas into methanol in a gas phase, in which, in the conversion step (S6), the reaction is allowed to proceed by condensing a high-boiling-point component containing methanol obtained as the result of the conversion and water and then discharging the condensed product to the outside of a reaction system.

12 Claims, 8 Drawing Sheets

(51) Int. Cl.

| | |
|---|---|
| ***C07C 29/151*** | (2006.01) |
| ***C10J 3/00*** | (2006.01) |

(56) References Cited

U.S. PATENT DOCUMENTS

| | | | | |
|---|---|---|---|---|
| 2012/0148472 | A1 | 6/2012 | Ahmed et al. | |
| 2019/0016655 | A1* | 1/2019 | Yiu ........................ | B01D 3/143 |
| 2019/0047931 | A1 | 2/2019 | Balthasar et al. | |
| 2022/0363617 | A1 | 11/2022 | Suzuta et al. | |

FOREIGN PATENT DOCUMENTS

| | | | |
|---|---|---|---|
| JP | 2007246486 | A | 9/2007 |
| JP | 2008201754 | A | 9/2008 |
| JP | 2010013422 | A | 1/2010 |
| JP | 2011143370 | A | 7/2011 |
| JP | 2013502390 | A | 1/2013 |
| JP | 2019513816 | A | 5/2019 |
| WO | 2012017893 | A1 | 2/2012 |
| WO | 2021060145 | A1 | 4/2021 |

OTHER PUBLICATIONS

Machine translation of JP2005298413A, Oct. 27, 2005, pp. 11-14 (Year: 2005).*

Machine translation of JP2010013422A, Jan. 21, 2010, pp. 1-41 (Year: 2010).*

Machine translation of WO2012017893A1, Feb. 9, 2012, pp. 1-8 (Year: 2012).*

Extended European Search Report issued Dec. 19, 2024 in EP Application No. 21861749.6.

* cited by examiner

METHOD FOR PRODUCING METHANOL

CROSS-REFERENCE TO RELATED APPLICATIONS

This application is a Section 371 of International Application No. PCT/JP2021/031683, filed Aug. 30, 2021, which was published in the Japanese language on Mar. 3, 2022 under International Publication No. WO 2022/045328 A1, which claims priority under 35 U.S.C. § 119 (b) to Japanese Application No. 2020-145859, filed Aug. 31, 2020, the disclosures of which are incorporated herein by reference in their entireties.

TECHNICAL FIELD

The present invention relates to a method for producing methanol from a waste material.

BACKGROUND ART

Combustible waste materials are usually treated by landfill or incineration. Not only incineration but also landfill is accompanied by discharge of carbon dioxide and heat. Therefore, improvement is required from the viewpoint of global environmental problems such as global warming countermeasures.

For the purpose of effectively utilizing waste materials in consideration of global environmental problems, there has been developed a method of converting waste materials into hydrogen, which is a high-energy substance, or methanol or dimethyl ether, which is one of the most basic organic substances. For example, Patent Document 1 discloses a waste material treatment system including a step of synthesizing methanol from hydrogen and carbon dioxide that are obtained by gasifying a waste material. Meanwhile, Patent Document 2 discloses a method for producing methanol by condensing a product obtained from a carbon oxide such as carbon dioxide and hydrogen.

PRIOR ART DOCUMENTS

Patent Documents

Patent Document 1: WO 2012-017893
Patent Document 2: JP-A-2005-298413

SUMMARY OF THE INVENTION

Problems to be Solved by the Invention

According to the system disclosed in Patent Document 1, however, the synthesis of methanol from carbon dioxide is not necessarily carried out sufficiently efficiently due to equilibrium constraints. Meanwhile, in the production of methanol disclosed in Patent Document 2, hydrogen used as a raw material is currently industrially produced by steam reforming of natural gas in many cases, and is generally derived from fossil fuel. Therefore, the production method disclosed in Patent Document 2 is not necessarily sufficient for industrially and efficiently producing methanol using an environmentally friendly raw material.

An object of one aspect of the present invention is to industrially and efficiently produce methanol from a waste material.

Means for Solving the Problems

In order to solve the above-mentioned problems, a method for producing methanol according to one aspect of the present invention includes: a gas acquisition step of obtaining a gas containing a carbon oxide and hydrogen from a waste material; and a conversion step of bringing at least a portion of the gas into contact with a catalyst to convert the portion of the gas into methanol in a gas phase, and in the conversion step, a reaction is allowed to proceed by condensing a high-boiling-point component containing methanol obtained as a result of the conversion and water and then discharging a condensed product to an outside of a reaction system.

Effect of the Invention

According to one aspect of the present invention, methanol can be industrially and efficiently produced from a waste material.

MODES FOR CARRYING OUT THE INVENTION

First Embodiment

Figure 1:
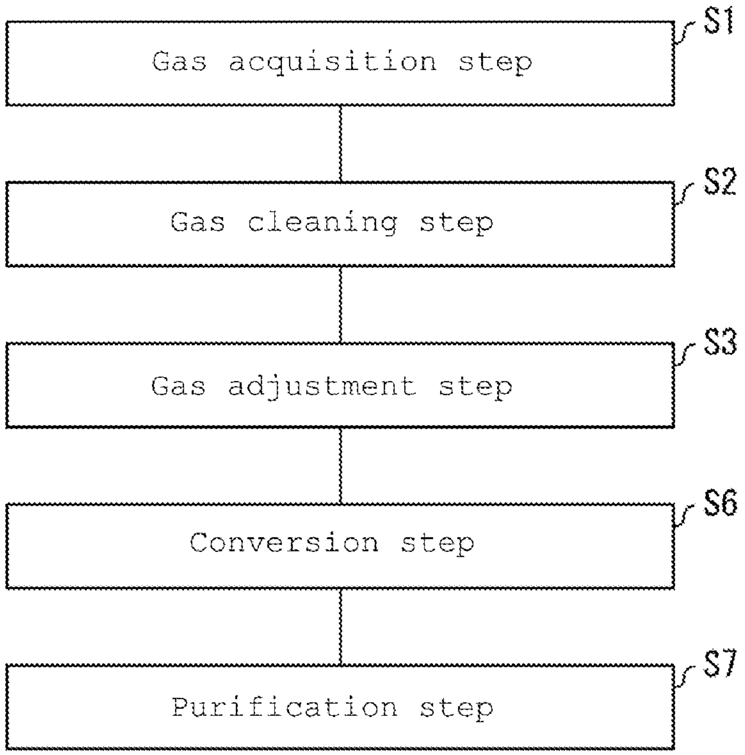
FIG. 1 is a flowchart illustrating an example of a method for producing methanol according to a first embodiment of the present invention.

Hereinafter, a method for producing methanol according to an embodiment of the present invention will be described in detail with reference to the drawings together with a production apparatus used for the method. Note that the drawings used below are used to illustrate the present invention, and dimensions in the drawings may be different from actual dimensions.

FIG. 1 is a flowchart illustrating an example of the method for producing methanol according to the present embodiment. As illustrated in FIG. 1, the method for producing methanol of the present invention includes a gas acquisition step S1 of decomposing a waste material to yield a gas containing a carbon oxide and hydrogen ($H_2$) (the gas is referred to as a waste material-derived gas G1), that is, gasification, and a conversion step S6 of synthesizing, using the gas as a source gas, methanol from at least a portion of the carbon oxide and hydrogen contained in the source gas. Here, the carbon oxide contains at least one of carbon monoxide (CO) and carbon dioxide ($CO_2$), and when the carbon oxide contains both, the abundance ratio between them is not particularly limited.

The flowchart illustrated in FIG. 1 includes a gas cleaning step S2, a gas adjustment step S3, and a purification step S7 in addition to the gas acquisition step S1 and the conversion step S6. The steps will be described in detail below. In the present embodiment, as an example, the flowchart illustrated in FIG. 1 and a methanol production apparatus (hereinafter simply referred to as a "production apparatus") that realizes the production flow illustrated in the flowchart will be described. The gas cleaning step S2, the gas adjustment step S3, and the purification step S7 are steps that can be incorporated into the production flow as necessary. The steps and the like illustrated in the drawings of the present description show only typical examples and do not limit the scope of the present invention in any way.

(Configuration of Methanol Production Apparatus)

Figure 2:
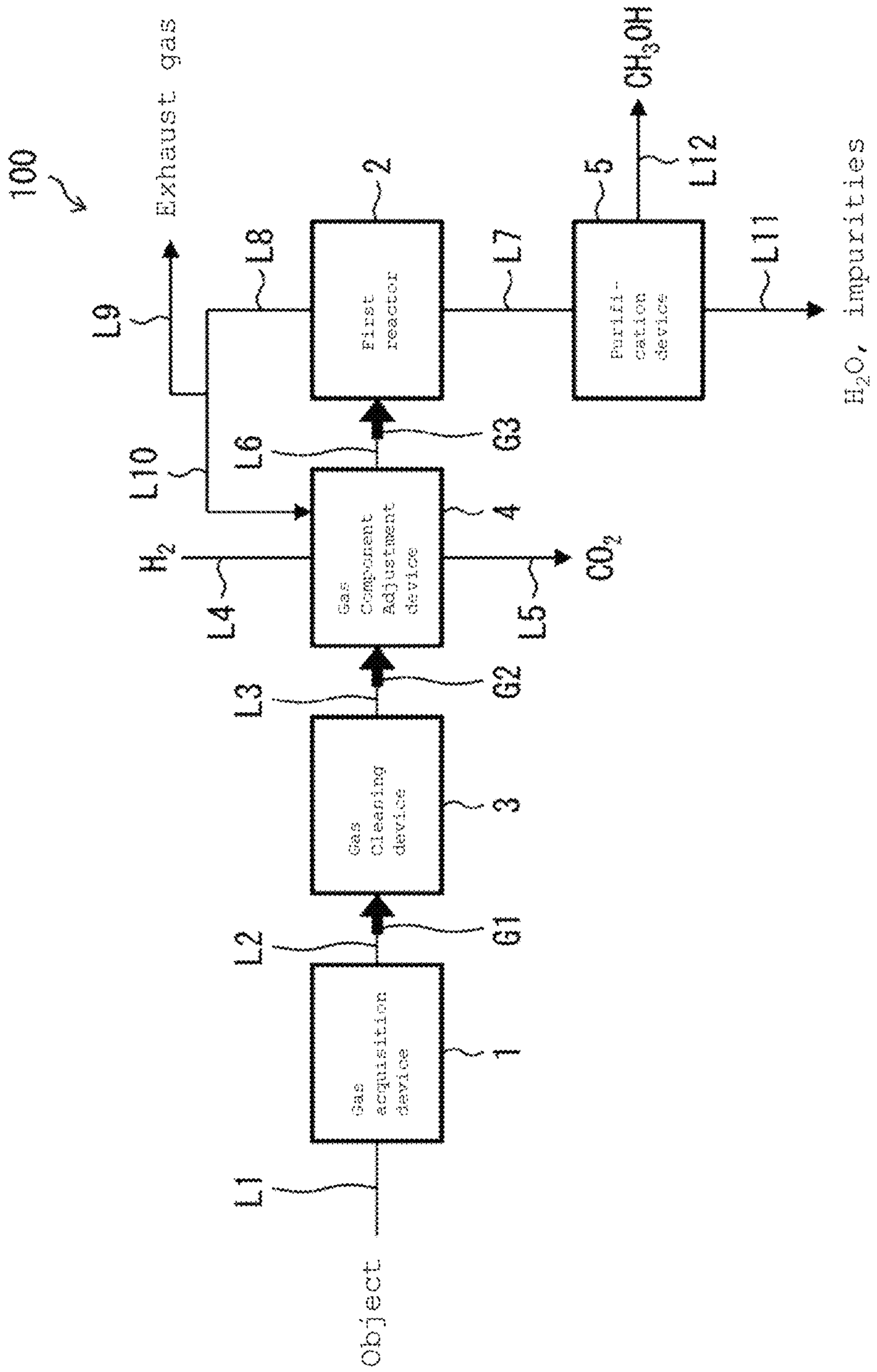
FIG. 2 is a system diagram schematically illustrating a configuration of a methanol production apparatus according to the first embodiment of the present invention.

First, an example of a configuration of a production apparatus 100 according to an embodiment to which the present invention is applied will be described. FIG. 2 is a system diagram schematically illustrating a configuration of the production apparatus 100 according to the first embodiment.

As illustrated in FIG. 2, the production apparatus 100 of the present embodiment has a schematic configuration including a gas acquisition device 1, a gas cleaning device 3, a gas component adjustment device 4, a first reactor 2, a purification device 5, and paths L1 to L12. The production apparatus 100 of the present embodiment is an apparatus for producing methanol from a waste material. The method for producing methanol of the present invention is a method of supplying a gas containing a carbon oxide and hydrogen, which is obtained by decomposing a waste material, as a source gas to the first reactor 2, and performing a reaction of converting the gas into methanol.

In the present embodiment, the waste material is required to be a material which contains an organic substance and from which a gas containing hydrogen and a carbon oxide is obtained in the gas acquisition step 31. Examples of the waste material include waste materials such as garbage, paper waste, fiber waste, plastic waste, sewage sludge, human waste, livestock waste, waste oil, rubber tires, black liquor, waste molasses, and mixtures thereof.

The gas acquisition device 1 is a device for performing the gas acquisition step S1 of decomposing a waste material (object) to acquire a gas containing a carbon oxide and hydrogen (the gas is referred to as the waste material-derived gas G1). The gas acquisition device 1 causes a waste material supplied from a waste material supply path L1 to react in the device. As the gas acquisition device 1, a known device such as a fixed bed furnace, a fluidized bed furnace, a bubbling fluidized bed furnace, a circulating fluidized bed furnace, or a circulating moving bed furnace can be used.

A waste material-derived gas G1 supply path L2 is provided between the gas acquisition device 1 and the gas cleaning device 3. Therefore, the waste material-derived gas G1 is supplied to the gas cleaning device 3.

The gas cleaning device 3 is a device that performs the gas cleaning step S2 of cleaning the waste material-derived gas G1 by removing impurities from the gas. The gas cleaning step S2 can be performed by a known method, and a known apparatus such as a wet cleaning tower or an electric dust collector can be used as the gas cleaning device 3.

A cleaned gas supply path L3 is provided between the gas cleaning device 3 and the gas component adjustment device 4. Therefore, a cleaned gas G2 that is the gas cleaned by the gas cleaning device 3 is supplied to the gas component adjustment device 4.

The gas component adjustment device 4 is a device that performs the gas adjustment step S3 of adjusting the component of the source gas supplied to the first reactor 2. The gas component adjustment device 4 is provided with a hydrogen supply path L4, and hydrogen can be supplied to the gas component adjustment device 4. The gas component adjustment device 4 is also provided with a carbon dioxide discharge path L5, and carbon dioxide can be discharged from the gas component adjustment device 4. The gas adjustment performed in the gas component adjustment device 4 will be described in detail in the following description of the gas component adjustment step.

A source gas supply path L6 is provided between the gas component adjustment device 4 and the first reactor 2. Therefore, an adjusted gas G3, which is the gas adjusted in the gas component adjustment device 4, is supplied to the first reactor 2 as the source gas. The gas supplied to the first reactor 2 as the source gas may be the waste material-derived gas G1 or the cleaned gas G2 depending on the configuration of the production apparatus.

Figure 3:
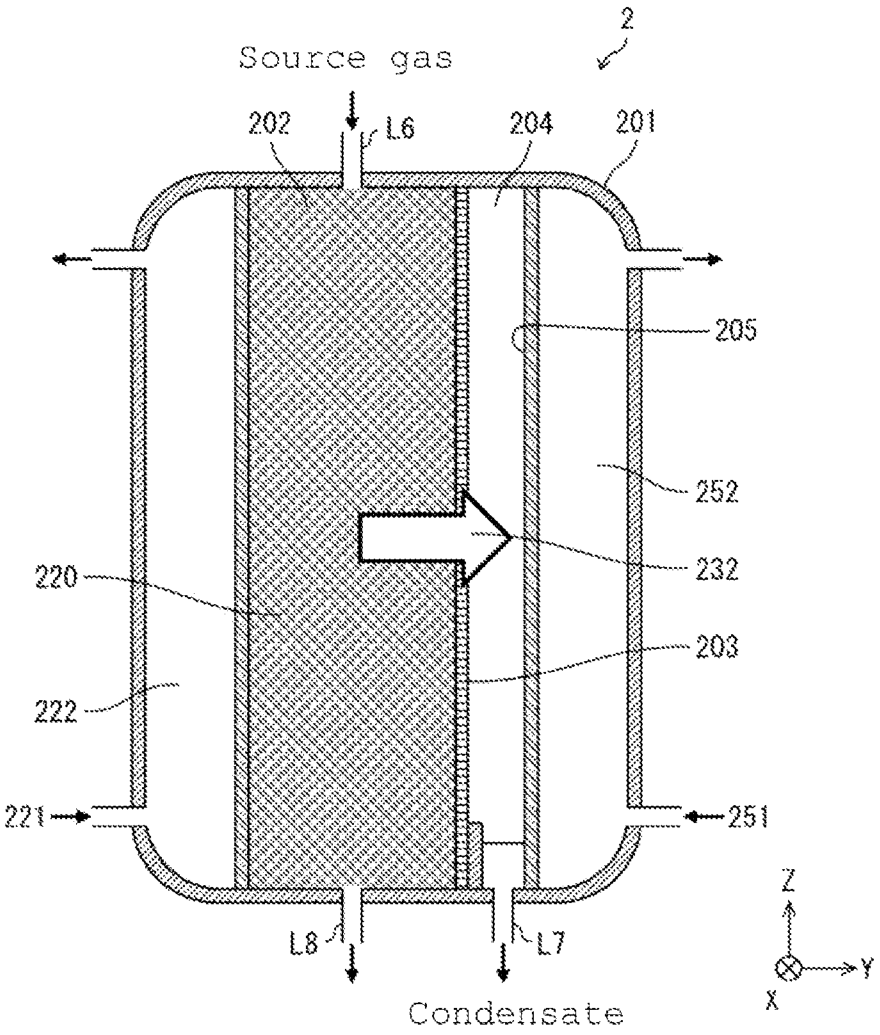
FIG. 3 is a cross-sectional view of an exemplary first reactor taken along a plane perpendicular to a bottom surface.

The first reactor 2 is a reactor that performs the conversion step S6 by causing a gas containing a carbon oxide and hydrogen supplied as a source gas to react in the presence of a catalyst to convert the gas into methanol. FIG. 3 is a cross-sectional view of an exemplary first reactor 2 taken along a plane perpendicular to a bottom surface.

As illustrated in FIG. 3, the first reactor 2 includes a reaction vessel 201, a catalyst layer 202, a permeation wall 203, and a condensing surface 205 disposed to be separated from the permeation wall 203 by a space 204. The reaction vessel 201 is, for example, a pressure-resistant metal vessel made of stainless steel. The catalyst layer 202 is a region where the source gas and a catalyst 220 come into contact with each other and the reaction is allowed to proceed. The catalyst layer 202 is filled with the catalyst 220 suitable for the reaction. The permeation wall 203 is made of a porous member through which a gas can permeate. A member used as the permeation wall 203 is a member through which a reaction gas 232 generated by the reaction in the catalyst layer 202 can pass and through which the catalyst 220 cannot pass. The space 204 is a space formed between the permeation wall 203 and the condensing surface 205. The condensing surface 205 is a surface that cools the reaction gas 232 that has passed through the permeation wall 203 to a temperature equal to or lower than a dew point of the reaction gas 232 to condense a high-boiling-point component containing methanol and water. The high-boiling-point component means a component having a high boiling point, and in the present description, means a component having a high boiling point among components contained in the reaction gas generated in the methanol conversion reaction. That is, in the present description, the high-boiling-point component is a component that condenses at a temperature equal to or lower than the dew point of the reaction gas generated in the methanol conversion reaction, and contains methanol and water.

The first reactor 2 may be provided with a first heating medium region 252 in which a first heating medium 251 is circulated in order to maintain the condensing surface 205 at a temperature equal to or lower than the dew point of the reaction gas 232. The first reactor 2 may also be provided with a second heating medium region 222 in which a second heating medium 221 for recovering heat generated by the reaction in the catalyst layer 202 is circulated.

A condensate recovery path L7 is provided between the first reactor 2 and the purification device 5. Therefore, the condensate containing methanol and water obtained by condensation in the first reactor 2 is discharged to the outside of the reaction system and supplied to the purification device 5.

The purification device 5 is a device that performs the purification step S7 of purifying methanol by generating the condensate to separate water and impurities. The condensate obtained from the first reactor 2 is obtained as a liquid mixture containing methanol and water as products. The method for extracting methanol from the mixture in the purification device 5 is not particularly limited. For example, it is possible to remove water and impurities through dehydration and purification treatment by a known method to obtain methanol. Examples of the dehydration and purification treatment method include distillation and membrane separation.

An unreacted gas resupply path L10 may be provided between the first reactor 2 and the gas component adjustment device 4. Therefore, the carbon oxide and/or hydrogen not reacted in the conversion step S6 in the first reactor 2 may be recovered as an unreacted gas, returned to the gas component adjustment device 4, and reused. The first reactor 2 may be provided with an exhaust gas discharge path L9. Therefore, the unreacted gas can be discharged as exhaust gas. Incidentally, after being recovered as necessary and before being discharged as exhaust gas, the unreacted gas may be burned and used as thermal energy used in the conversion step S6 into methanol.

(Method for Producing Methanol)

The method for producing methanol according to the first embodiment is performed, for example, according to the flowchart illustrated in FIG. 1. Note that the flowchart illustrated in FIG. 1 is an example, and the present invention is not limited thereto. The steps in the method for producing methanol according to the first embodiment will be described in detail.

(Gas Acquisition Step S1)

The gas acquisition step S1 is a step of obtaining a gas containing a carbon oxide and hydrogen from a waste material. When a waste material containing an unsaturated hydrocarbon component, such as plastic waste, is used as the waste material, it is assumed that, for example, reactions represented by the following formulae (1) to (4) occur in the gas acquisition device 1 due to a reaction between a hydrocarbon and water vapor or oxygen.

$$CnH_2n+nH_2O \rightarrow nCO+2nH_2 \quad (1)$$

$$CnH_2n+2nH_2O \rightarrow nCO_2+3nH_2 \quad (2)$$

$$CnH_2n+0.5nO_2 \rightarrow nCO+nH_2 \quad (3)$$

$$CnH_2n+nO_2 \rightarrow nCO_2+nH_2 \quad (4)$$

In the formulae (1) and (3), carbon monoxide is produced together with hydrogen. In the method for producing methanol of the present invention, a step of obtaining carbon dioxide and hydrogen by a reaction of the following formula (5) may be performed using the carbon monoxide and water as raw materials. In addition, a step of obtaining thermal energy and carbon dioxide required for a gasification reaction (gas acquisition reaction) by a reaction of the following formula (6) may be performed using the carbon monoxide and oxygen as raw materials.

$$CO+H_2O \rightarrow CO_2+H_2 \quad (5)$$

$$CO+0.5O_2 \rightarrow CO_2 \quad (6)$$

In the reactions of the formulae (1) to (6), 1 to 3 mol of hydrogen is obtained per 1 mol of carbon atoms.

Meanwhile, when a waste material containing a naturally occurring organic substance is used as the waste material, it is considered that, for example, a reaction represented by the following formula (7) and/or a reaction represented by the following formula (8) occurs in the gas acquisition device 1.

$$(C_6H_{12}O_6)n \rightarrow 6nCO+6nH_2 \quad (7)$$

$$(C_6H_{12}O_6)n+6nH_2O \rightarrow 6nCO_2+12nH_2 \quad (8)$$

In the formula (7), carbon monoxide is produced together with hydrogen. The carbon monoxide and water may be used as raw materials to yield carbon dioxide and hydrogen by the reaction of the formula (5). In the formulae (7) and (8), 1 to 2 mol of hydrogen is obtained per 1 mol of carbon atoms.

In the reaction of obtaining carbon monoxide and hydrogen from the organic substance as described above, a reaction at a high temperature may be required as compared with a reaction of obtaining carbon dioxide and hydrogen. Therefore, a method of obtaining carbon dioxide and hydrogen is expected to be more advantageous in view of energy cost related to temperature increase.

(Gas Cleaning Step S2)

The gas cleaning step S2 is a step of cleaning the gas by removing impurities from the waste material-derived gas G1. The waste material-derived gas G1 may contain, as impurities, solid contents such as soot and fly ash that are catalyst-poisoning substances. The waste material-derived gas G1 may also contain, as other impurities, reaction inhibiting components such as a sulfur component and a nitrogen component. In such a case, it is preferable to subject the waste material-derived gas G1 to cleaning by the gas cleaning step S2 before supplying the waste material-derived gas G1 to the first reactor 2 in the subsequent stage. The gas cleaning step S2 is usually performed according to the solid content and the reaction inhibiting component contained in the waste material-derived gas G1, and is performed by a conventionally known cleaning method.

Cleaning the gas in the gas cleaning step S2 can reduce the degradation rate of the catalyst used in the conversion step S6 and extend the catalyst life.

(Gas Adjustment Step S3)

The gas adjustment step S3 is a step of adjusting the component of the gas to be subjected to the conversion step S6 described later. The amount of hydrogen required for the production of methanol is 2 mol per 1 mol of carbon monoxide (CO) and 3 mol per 1 mol of carbon dioxide ($CO_2$). Therefore, it is ideal that the volume fractions of hydrogen, carbon monoxide, and carbon dioxide in the source gas supplied to the first reactor 2 in the subsequent stage are adjusted so that the index SN represented by the following formula (9) is 2. In the following formula (9), $yH_2$, $yCO_2$, and $yCO$ are respectively volume fractions of hydrogen, carbon dioxide, and carbon monoxide in the source gas supplied to the first reactor 2.

$$SN=(yH_2-yCO_2)/(yCO+yCO_2) \quad (9)$$

Meanwhile, in general, in order to perform gasification without inputting thermal energy from the outside even when a high energy waste material such as a polyolefin is used as a waste material, it may be necessary to secure thermal energy by the oxidation reaction of carbon monoxide illustrated in the formula (6). Since the percentage of carbon dioxide increases by the reaction of the formula (6), the index SN represented by the formula (9) gets closer to about 1.

In the method for producing methanol of the present invention, when the waste material-derived gas G1 obtained in the gas acquisition step S1 contains hydrogen, carbon dioxide, and carbon monoxide, the three components can be supplied to the first reactor 2. However, when the value of the index SN is low, it is preferable to add a gas adjustment step of adjusting the SN value in advance before supplying the waste material-derived gas G1 as a source gas to the first reactor 2. The value of the index SN is preferably 1 or more and 10 or less, and more preferably adjusted to 1.5 or more and 3 or less.

An example of a method of adjusting the value of the index SN in the gas adjustment step S3 is a method of removing at least a portion of carbon dioxide from the waste material-derived gas G1 obtained in the gas acquisition step S1. The carbon dioxide removed here may be used for another application. Specifically, for example, the waste material-derived gas G1 can be treated by a chemical absorption method using an amine solution to remove carbon dioxide as an acidic gas, so that a gas containing hydrogen and carbon monoxide can be obtained. Besides the chemical absorption method, treatment by a cryogenic separation method can separate carbon dioxide having the highest boiling point among the three components to yield a gas containing hydrogen and carbon monoxide. In addition, carbon dioxide may be separated by a membrane separation method using a separation membrane that selectively inhibits carbon dioxide, or more preferably a separation membrane that is selectively permeable to carbon dioxide.

Another example of the method of adjusting the value of the index SN in the gas adjustment step S3 is a method of adding (additionally supplying) hydrogen (hydrogen gas) to the waste material-derived gas G1 obtained in the gas acquisition step S1. As a method for obtaining the hydrogen, for example, known techniques such as reaction by reforming or decomposition of fossil fuel, thermal decomposition reaction or dehydrogenation reaction of a hydrocarbon, electrolysis of water or salt water, decomposition of water using a photocatalyst, and decomposition of ammonia can be used.

Examples of the thermal decomposition reaction of a hydrocarbon include a method of producing a lower olefin or the like by a thermal decomposition reaction of naphtha, and a method of obtaining hydrogen by thermal decomposition of methane. Examples of the dehydrogenation reaction of a hydrocarbon include a method of producing ethylene by a dehydrogenation reaction of ethane, a method of producing propylene by a dehydrogenation reaction of propane, a method of producing toluene by a dehydrogenation reaction of methylcyclohexane, and a method of producing cyclohexanone by a dehydrogenation reaction of cyclohexanol.

As still another method of adjusting the value of the index SN in the gas adjustment step S3, at least a portion of a carbon oxide contained in the waste material-derived gas G1 obtained in the gas acquisition step S1 may be reformed, decomposed, or the like to change the ratio between carbon monoxide and carbon dioxide contained in the waste material-derived gas G1.

The gas adjustment step S3 may be performed by at least one of (i) a treatment of adding hydrogen to the gas, (ii) a treatment of removing at least a portion of carbon dioxide from the gas, and (iii) a treatment of decomposing or reforming at least a portion of the carbon oxide in the gas.

Adjusting the component of the gas in the gas adjustment step S3 can adjust the raw material composition so as to be a composition suitable for the methanol conversion reaction (synthesis reaction) in the subsequent conversion step S6. Therefore, the conversion rate into methanol in the conversion step S6 can be improved.

(Conversion Step S6)

The conversion step S6 is a step of bringing at least a portion of the gas acquired from the waste material into contact with a catalyst to convert the portion of the gas into methanol in a gas phase. In the conversion step S6, a reaction is allowed to proceed by condensing a high-boiling-point component containing methanol obtained as a result of the conversion and water and then discharging a condensed product to the outside of the reaction system. Therefore, the carbon oxide and hydrogen can be converted until the conversion rate reaches an equilibrium conversion rate or more. Here, the equilibrium conversion rate means an equilibrium conversion rate of the carbon oxide in the source gas based on at least one of carbon and hydrogen, and is calculated from an equilibrium composition according to the reaction temperature and pressure.

Then, the catalyst 220 used in the conversion step S6 will be described. In the case of obtaining methanol by the reaction between carbon dioxide and hydrogen, water is produced as a by-product as represented by the following formula (10). Meanwhile, in the case of obtaining methanol by the reaction between carbon monoxide and hydrogen, water is not produced as a by-product as represented by the following formula (11).

$$CO_2+3H_2 \rightarrow CH_3OH+H_2O \text{ (49.4 kJ/mol (exothermic reaction))} \quad (10)$$

$$CO+2H_2 \rightarrow CH_3OH \text{ (90.4 kJ/mol (exothermic reaction))} \quad (11)$$

Water produced as a by-product in the reaction of the formula (10) may lower the reaction activity of the catalyst and lower the productivity of methanol. Therefore, in the method for producing methanol of the present invention, it is preferable to use a catalyst that is hardly affected by water.

Therefore, in the present embodiment, it is preferable to use, as the catalyst 220, a catalyst that is less likely to cause a decrease in activity due to water, for example, a copper-based catalyst. As the catalyst 220, for example, a catalyst that contains copper, zinc, aluminum, and silicon as essential components and can contain zirconium, palladium, and gallium as optional components is used. In general, a catalyst used for obtaining methanol by the reaction of carbon dioxide and hydrogen tends to be capable of yielding methanol also when carbon monoxide and hydrogen are used as raw materials. Therefore, the catalyst containing a component such as copper can be suitably used in the method for producing methanol of the present embodiment for the reason that the catalyst exhibits activity for both the reaction between carbon dioxide and hydrogen and the reaction between carbon monoxide and hydrogen, and also exhibits durability against water produced as a by-product.

When a copper-containing catalyst is used as the catalyst 220, the particle size thereof is not particularly limited, and may be, for example, 1 mm or more and 20 mm or less, 2 mm or more and 20 mm or less, 3 mm or more and 20 mm or less, 3 mm or more and 15 mm or less, or 3 mm or more and 10 mm or less. When the particle size of the catalyst 220 is within the above-mentioned range, the catalyst 220 is suitable not only for ease of handling but also from the viewpoint of the strength, and is further suitable for loading the catalyst 220 in a fixed bed to form the catalyst layer 202. The method for producing the catalyst 220 having the above-mentioned particle size is not particularly limited, and a known method can be used. A tableting method is suitably used.

The reaction temperature in the catalyst layer 202 may be, for example, about 180° C. or more and 260° C. or less, and is preferably 220° C. or more and 240° C. or less. The reaction pressure may be, for example, about 0.2 MPaG or more and 10 MPaG or less, and is preferably 1 MPaG or more and 5 MPaG or less.

With use of the first reactor 2, based on at least one of the carbon oxide and hydrogen in the source gas supplied to the first reactor 2, 60% or more, preferably 70% or more, more preferably 80% or more, and still more preferably 90% or more of the component is converted into methanol. When the carbon oxide contains both carbon monoxide and carbon dioxide, the conversion rate here is calculated based on at least one of carbon monoxide, carbon dioxide, and hydrogen. Therefore, it is possible to generate methanol beyond the equilibrium composition, and it is possible to reduce the facility scale per methanol generation amount.

The conversion step in the first reactor 2 may be performed in the presence of a so-called inert gas that is not involved in the conversion reaction or the decrease in the activity of the catalyst.

In the present embodiment, the waste material-derived gas G1 obtained in the gas acquisition step S1 can be used as a source gas in the conversion step S6. In the conversion step S6, a portion or all of carbon monoxide, carbon dioxide, and hydrogen in the source gas are used. Meanwhile, carbon dioxide or hydrogen obtained outside the production apparatus may be added to the waste material-derived gas G1 obtained in the gas acquisition step S1 to yield a source gas used in the conversion step S6. The method for obtaining carbon dioxide or hydrogen that can be added here is not particularly limited, and for example, carbon dioxide obtained when burning fossil fuel for power generation may be added. The gas adjustment step S3 may be performed after the gas acquisition step S1 and before the source gas is supplied to the first reactor 2 in which the conversion step S6 is performed, or may be performed simultaneously with the supply of the source gas. In addition, the gas adjustment step S3 may be performed in one step or in a plurality of steps.

According to one aspect of the present invention, methanol can be more efficiently produced from a waste material in a small-scale facility, and the waste material can be effectively utilized. It also contributes to the reduction of fossil fuel-derived carbon dioxide associated with conventional methanol production.

Second Embodiment

Another embodiment of the present invention will be described below. For convenience of description, members having the same functions as those of the members described in the above-mentioned embodiment are denoted by the same reference signs, and the description thereof will not be repeated.

Figure 4:
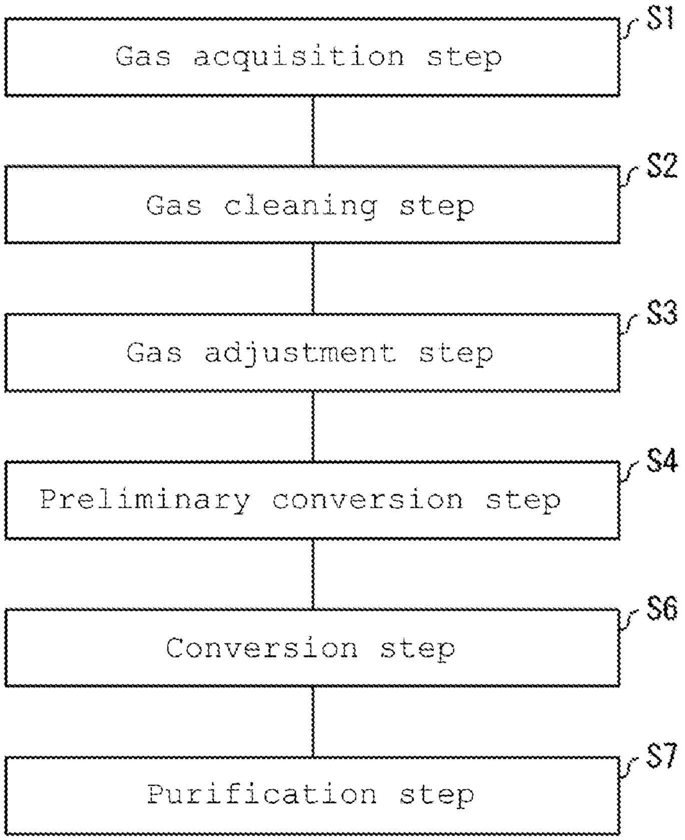
FIG. 4 is a flowchart illustrating an example of a method for producing methanol according to a second embodiment of the present invention.

FIG. 4 is a flowchart illustrating an example of a method for producing methanol according to the second embodiment. As illustrated in FIG. 4, the method for producing methanol according to the second embodiment is different from the first embodiment in that the method includes a preliminary conversion step S4 between the gas adjustment step S3 and the conversion step S6. The flowchart illustrated in FIG. 4 is an example, and the present invention is not limited thereto. For example, the gas adjustment step S3 may be moved to or added between the preliminary conversion step S4 and the conversion step S6.

Figure 5:
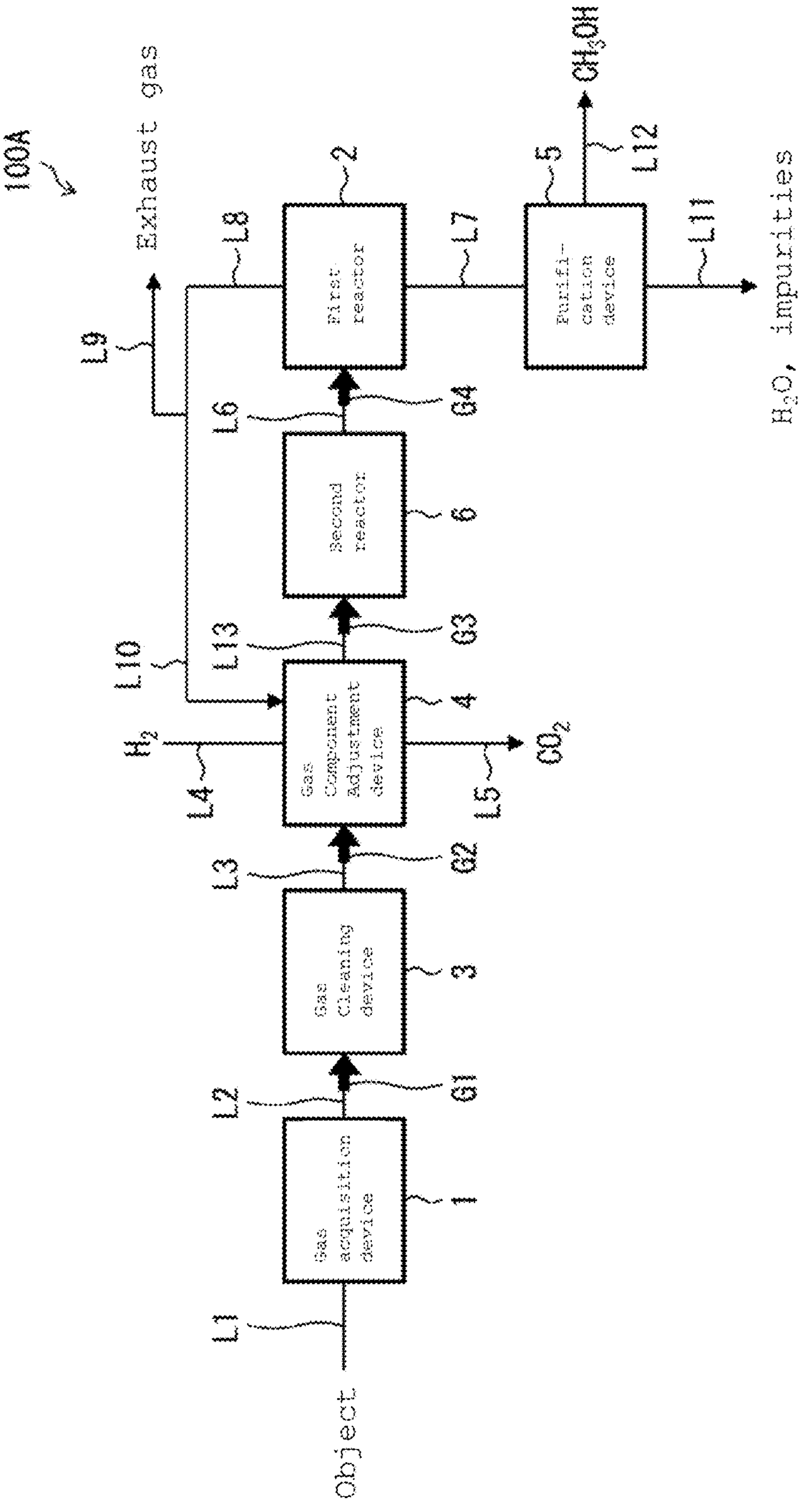
FIG. 5 is a system diagram schematically illustrating a configuration of a methanol production apparatus according to the second embodiment of the present invention.

FIG. 5 is a system diagram schematically illustrating a configuration of a methanol production apparatus (production apparatus 100A) according to the second embodiment. The production apparatus 100A has a schematic configuration including a gas acquisition device 1, a gas cleaning device 3, a gas component adjustment device 4, a first reactor 2, a purification device 5, a second reactor 6, and paths L1 to L13. The production apparatus 100A is similar to the production apparatus 100 of the first embodiment except that the production apparatus 100A further includes the second reactor 6 and a preliminary conversion source gas supply path L13.

The preliminary conversion source gas supply path L13 is provided between the gas component adjustment device 4 and the second reactor 6. Therefore, an adjusted gas G3, which is the gas adjusted in the gas component adjustment device 4, is supplied to the second reactor 6 as a preliminary conversion source gas.

The second reactor 6 is a reactor that performs the preliminary conversion step S4 of allowing a gas containing a carbon oxide and hydrogen supplied as a preliminary conversion source gas to proceed to an equilibrium composition of the methanol conversion reaction. The second reactor 6 may be, for example, a general fixed bed catalyst reactor filled with a solid catalyst or a reactor having the same structure as that of the first reactor 2. As described above, the first reactor 2 can allow the reaction to proceed beyond the equilibrium of the methanol conversion reaction. It is also possible to allow the reaction to proceed to the equilibrium composition in the second reactor 6 at a stage before the first reactor 2, and then supply a preliminarily converted gas G4 obtained in the reaction to the first reactor 2 as a source gas through a source gas supply path L6.

The method for producing methanol according to the second embodiment is performed, for example, according to the flowchart illustrated in FIG. 4. The description of the same steps as those of the first embodiment will be omitted, and the preliminary conversion step S4 will be described below.

(Preliminary Conversion Step S4)

The preliminary conversion step S4 is a step of allowing a gas containing a carbon oxide and hydrogen to proceed to an equilibrium composition of the methanol conversion reaction. It is preferable to convert, in the second reactor 6, the carbon oxide and hydrogen in the preliminary conversion source gas into methanol until the conversion rate reaches a predetermined conversion rate or more. The predetermined conversion rate is 80% of the equilibrium conversion rate of the carbon oxide in the preliminary conversion source gas based on carbon, and is calculated, for example, from the equilibrium composition according to the reaction temperature and pressure. In addition, it is more desirable to separate a high-boiling-point component containing methanol and water from the gas obtained in the second reactor 6, adjust the composition, and then supply the gas to the first reactor. Here, the equilibrium conversion rate means a conversion rate calculated from the equilibrium composition according to the reaction temperature and pressure. When a general solid catalyst reactor is used as the second reactor 6, it is not always necessary to condense water and methanol as products by cooling. In this case, it is also possible to recover reaction heat generated during the methanol conversion reaction from the carbon oxide and hydrogen at a higher temperature. When a mixed gas containing carbon monoxide and carbon dioxide is used as the preliminary conversion source gas, of the reactions of the formulae (10) and (11), the methanol conversion reaction from carbon monoxide represented by the formula (11) preferentially proceeds because of the equilibrium of the two reactions. Therefore, in the preliminary conversion step S4, more reaction heat can be recovered. An aspect in which a general solid catalyst reactor is employed as the second reactor 6 in the preliminary conversion step S4 is a preferable aspect from the viewpoint of effective use of thermal energy.

The reaction temperature in the catalyst layer of the second reactor 6 may be, for example, about 180° C. to 260° C., and is preferably 220° C. to 240° C. The reaction pressure may be, for example, about 0.2 MPaG or more and 10 MPaG or less, and is preferably 1 MPaG or more and 5 MPaG or less.

Allowing the reaction to proceed to the equilibrium composition in the preliminary conversion step S4 can allow the conversion of the carbon oxide and hydrogen beyond the equilibrium to proceed more rapidly in the conversion step S6. That is, performing the preliminary conversion step S4 can improve the efficiency of the conversion reaction in the conversion step S6.

Third Embodiment

Another embodiment of the present invention will be described below. For convenience of description, members having the same functions as those of the members described in the above-mentioned embodiments are denoted by the same reference signs, and the description thereof will not be repeated.

Figure 6:
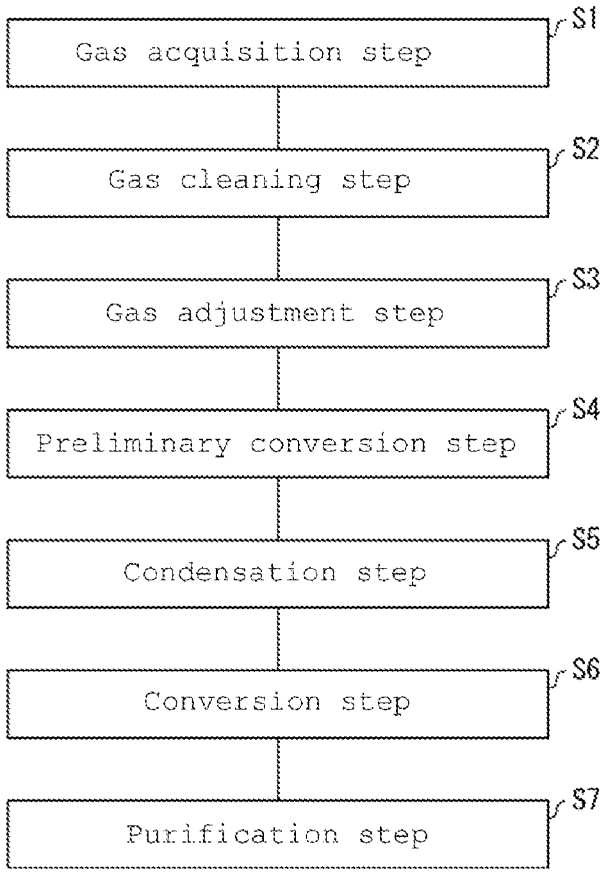
FIG. 6 is a flowchart illustrating an example of a method for producing methanol according to a third embodiment of the present invention.

FIG. 6 is a flowchart illustrating an example of a method for producing methanol according to the third embodiment. As illustrated in FIG. 6, the method for producing methanol according to the third embodiment is different from the second embodiment in that the method includes a condensation step S5 between the preliminary conversion step S4 and the conversion step S6. The flowchart illustrated in FIG. 6 is an example, and the present invention is not limited thereto. For example, the gas adjustment step S3 may be moved to or added between the preliminary conversion step S4 and the condensation step S5 and/or between the condensation step S5 and the conversion step S6.

Figure 7:
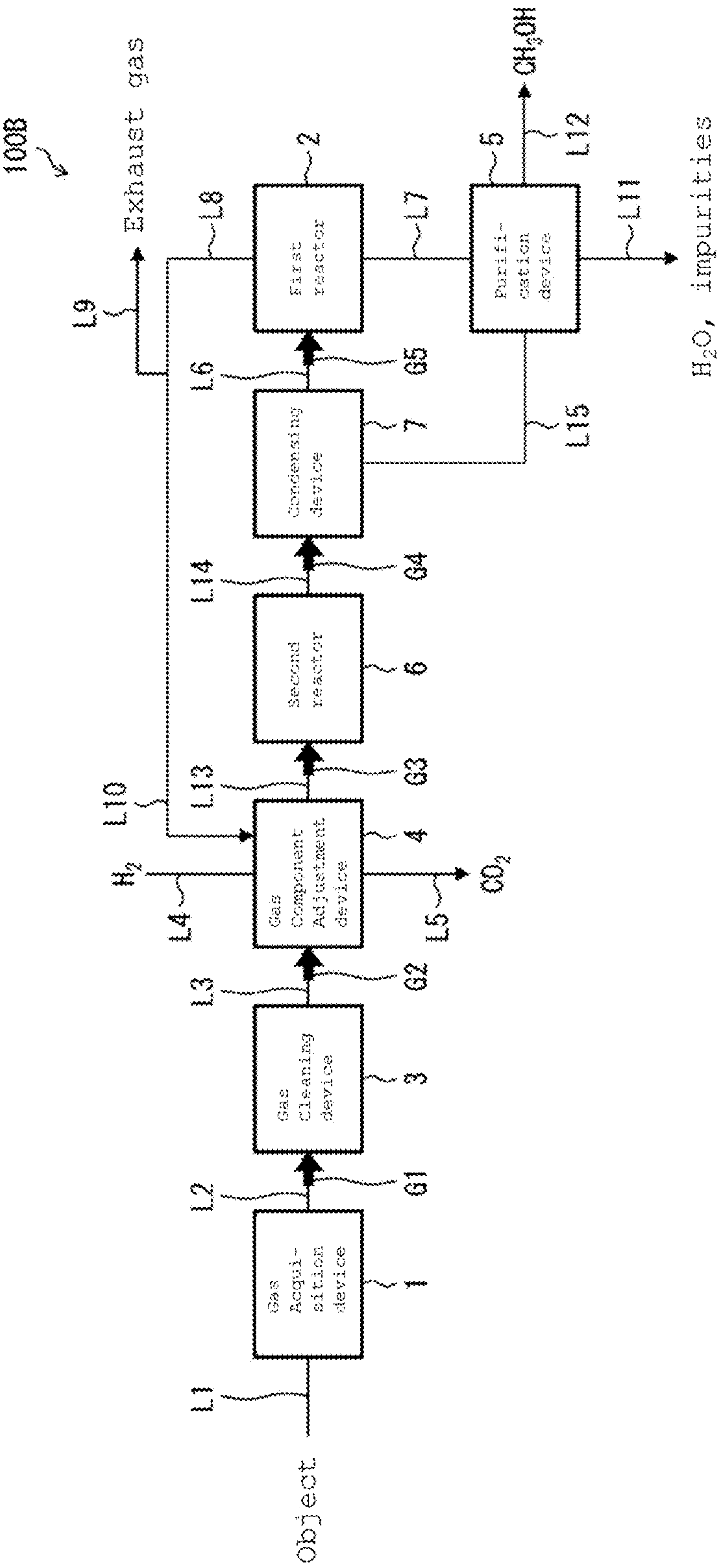
FIG. 7 is a system diagram schematically illustrating a configuration of a methanol production apparatus according to the third embodiment of the present invention.

FIG. 7 is a system diagram schematically illustrating a configuration of a methanol production apparatus (production apparatus 100B) according to the third embodiment. The production apparatus 100B has a schematic configuration including a gas acquisition device 1, a gas cleaning device 3, a gas component adjustment device 4, a first reactor 2, a purification device 5, a second reactor 6, a condensing device 7, and paths L1 to L15. The production apparatus 100B is similar to the production apparatus 100A of the second embodiment except that the production apparatus 100B further includes the condensing device 7, a preliminarily converted gas supply path L14, and a condensate recovery path L15.

The preliminarily converted gas supply path L14 is provided between the second reactor 6 and the condensing device 7. Therefore, the preliminarily converted gas G4 that is the reaction gas preliminarily converted by the second reactor 6 is supplied to the condensing device 7.

The condensing device 7 is a device that condenses a high-boiling-point component contained in the preliminarily converted gas G4. As the condensing device 7, a known condensing device (condenser) can be used. The condensate recovery path L15 is provided between the condensing device 7 and the purification device 5. Therefore, the condensate obtained by condensation in the condensing device 7 is supplied to the purification device 5 and purified.

A source gas supply path L6 is provided between the condensing device 7 and the first reactor 2. Therefore, a post-condensation-step gas G5 after being subjected to the condensation treatment by the condensing device 7 can be supplied to the first reactor 2 as a source gas.

The method for producing methanol according to the third embodiment is performed, for example, according to the flowchart illustrated in FIG. 6. The description of the same steps as those of the first and second embodiments will be omitted, and the condensation step S5 will be described below.

(Condensation Step S5)

The condensation step S5 is a step of condensing a high-boiling-point component contained in the preliminarily converted gas G4. The high-boiling-point component contains water and methanol. The condensation step S5 can condense the high-boiling-point component contained in the preliminarily converted gas G4 and discharge the condensed product to the outside of the reaction system. Therefore, the conversion of the carbon oxide and hydrogen beyond the equilibrium in the conversion step S6 can be realized by condensation of a smaller amount of the high-boiling-point component. Therefore, the first reactor 2 can be downsized.

The present invention is not limited to the above-described embodiments, and various modifications can be made within the scope indicated in the claims, and embodiments obtained by appropriately combining technical means disclosed in different embodiments are also included in the technical scope of the present invention.

EXAMPLES

Hereinafter, examples of the method for producing methanol according to the above-described embodiments, which are within the scope of the present invention (Examples 1, 2, and 3), and an example of the method for producing methanol, which is outside the scope of the present invention (comparative example) will be described.

Example 1

In Example 1, a specific example of the method for producing methanol according to the first embodiment will be described. That is, according to the flowchart of FIG. 1, the method for producing methanol performed using the above-described production apparatus 100 illustrated in FIG. 2 will be described. Note that members having the same functions as those of the members described in the above-mentioned embodiment are denoted by the same reference signs, and the description thereof will not be repeated. The same applies to other examples.

In the production apparatus 100, a waste material as an object is supplied to the gas acquisition device 1 via the path L1, and the waste material-derived gas G1 is obtained (the gas acquisition step S1). The composition of the waste material-derived gas G1 obtained in the gas acquisition step S1 is 45 vol % of $H_2$, 30 vol % of CO, 20 vol % of $CO_2$, and 5 vol % of $N_2$.

The obtained waste material-derived gas G1 is supplied to the gas cleaning device 3 via the path L2, and the cleaned gas G2 is obtained (the gas cleaning step S2).

The obtained cleaned gas G2 is supplied to the gas component adjustment device 4 via the path L3. In addition, the unreacted gas circulated from the downstream first reactor 2 is supplied to the gas component adjustment device 4 via the path L10. The index SN of the adjusted gas G3 discharged from the gas component adjustment device 4 is adjusted to 2 by the addition of $H_2$ via the path L4 (the gas adjustment step S3).

The adjusted gas G3 having the adjusted index SN is supplied to the first reactor 2 via the path L6 and converted into methanol and water (the conversion step S6). In the conversion step S6, the reaction is allowed to proceed by condensing the generated methanol and water and then discharging the condensed product to the outside of the reaction system.

The unreacted gas is discharged from the first reactor 2 via the path L8. Of the discharged unreacted gas, 50% is returned to the gas component adjustment device 4 via the path L10 and reused, and the remaining 50% is discharged as exhaust gas via the path L9.

The condensate obtained by condensation in the first reactor 2 is supplied to the purification device 5 via the path L7. Water and impurities removed from the supplied condensate are discharged via the path L11, and purified methanol is obtained via the path L12 (the purification step S7).

According to the present example, methanol can be synthesized by acquiring the waste material-derived gas G1 from the waste material, and using the gas as a source gas. Further, according to the present example, methanol is obtained at a yield of 88.3% based on carbon atoms of the carbon oxide contained in the waste material-derived gas G1 obtained in the gas acquisition device 1.

Example 2

In Example 2, a specific example of the method for producing methanol according to the second embodiment will be described. That is, according to the flowchart of FIG. 4, the method for producing methanol performed using the above-described production apparatus 100A illustrated in FIG. 5 will be described.

In the production apparatus 100A, a waste material as an object is supplied to the gas acquisition device 1 via the path L1, and the waste material-derived gas G1 is obtained (the gas acquisition step S1). The composition of the waste material-derived gas G1 obtained in the gas acquisition step S1 is 45 vol % of $H_2$, 30 vol % of CO, 20 vol % of $CO_2$, and 5 vol % of $N_2$.

The obtained waste material-derived gas G1 is supplied to the gas cleaning device 3 via the path L2, and the cleaned gas G2 is obtained (the gas cleaning step S2).

The obtained cleaned gas G2 is supplied to the gas component adjustment device 4 via the path L3. In addition, the unreacted gas circulated from the downstream first reactor 2 is supplied to the gas component adjustment device 4 via the path L10. The index SN of the adjusted gas G3 discharged from the gas component adjustment device 4 is adjusted to 2 by the addition of $H_2$ via the path L4 (the gas adjustment step S3).

The adjusted gas G3 having the adjusted index SN is supplied to the second reactor 6 via the path L13 and converted into methanol and water (the preliminary conversion step S4). In the preliminary conversion step S4, the reaction is allowed to proceed until the conversion rate reaches an equilibrium conversion rate that is calculated from the equilibrium composition according to the reaction temperature and pressure.

The preliminarily converted gas G4 obtained through the preliminary conversion step S4 is supplied to the first reactor 2 via the path L6 and converted into methanol and water (the conversion step S6). In the conversion step S6, the reaction is allowed to proceed by condensing the generated methanol and water and then discharging the condensed product to the outside of the reaction system.

The unreacted gas is discharged from the first reactor 2 via the path L8. Of the discharged unreacted gas, 50% is returned to the gas component adjustment device 4 via the path L10 and reused, and the remaining 50% is discharged as exhaust gas via the path L9.

The condensate obtained by condensation in the first reactor 2 is supplied to the purification device 5 via the path L7. Water and impurities removed from the supplied condensate are discharged via the path L11, and purified methanol is obtained via the path L12 (the purification step S7).

According to the present example, methanol can be synthesized by acquiring the waste material-derived gas G1 from the waste material, and using the gas as a source gas. Further, according to the present example, methanol is obtained at a yield of 88.3% based on carbon atoms of the carbon oxide contained in the waste material-derived gas G1 obtained in the gas acquisition device 1.

Example 3

In Example 3, a specific example of the method for producing methanol according to the third embodiment will be described. That is, according to the flowchart of FIG. 6, the method for producing methanol performed using the above-described production apparatus 100B illustrated in FIG. 7 will be described.

In the production apparatus 100B, a waste material as an object is supplied to the gas acquisition device 1 via the path L1, and the waste material-derived gas G1 is obtained (the gas acquisition step S1). The composition of the waste material-derived gas G1 obtained in the gas acquisition step S1 is 45 vol % of $H_2$, 30 vol % of CO, 20 vol % of $CO_2$, and 5 vol % of $N_2$.

The obtained waste material-derived gas G1 is supplied to the gas cleaning device 3 via the path L2, and the cleaned gas G2 is obtained (the gas cleaning step S2).

The obtained cleaned gas G2 is supplied to the gas component adjustment device 4 via the path L3. In addition, the unreacted gas circulated from the downstream first reactor 2 is supplied to the gas component adjustment device 4 via the path L10. The index SN of the adjusted gas G3 discharged from the gas component adjustment device 4 is adjusted to 2 by the addition of $H_2$ via the path L4 (the gas adjustment step S3).

The adjusted gas G3 having the adjusted index SN is supplied to the second reactor 6 via the path L13 and converted into methanol and water (the preliminary conversion step S4). In the preliminary conversion step S4, the reaction is allowed to proceed until the conversion rate reaches an equilibrium conversion rate that is calculated from the equilibrium composition according to the reaction temperature and pressure.

The preliminarily converted gas G4 obtained through the preliminary conversion step S4 is supplied to the condensing device 7 via the path L14, and methanol and water are condensed (the condensation step S5).

The post-condensation-step gas G5 obtained through the condensation step S5 is supplied to the first reactor 2 via the path L6 and converted into methanol and water (the conversion step S6). In the conversion step S6, the reaction is allowed to proceed by condensing the generated methanol and water and then discharging the condensed product to the outside of the reaction system.

The unreacted gas is discharged from the first reactor 2 via the path L8. Of the discharged unreacted gas, 50% is returned to the gas component adjustment device 4 via the path L10 and reused, and the remaining 50% is discharged as exhaust gas via the path L9.

The condensate obtained by condensation in the first reactor 2 is supplied to the purification device 5 via the path L7. In addition, the condensate obtained by condensation in the condensing device 7 is supplied to the purification device 5 via the path L15. Water and impurities removed from the supplied condensate are discharged via the path L11, and purified methanol is obtained via the path L12 (the purification step S7).

According to the present example, methanol can be synthesized by acquiring the waste material-derived gas G1 from the waste material, and using the gas as a source gas. Further, according to the present example, methanol is obtained at a yield of 91.5% based on carbon atoms of the carbon oxide contained in the waste material-derived gas G1 obtained in the gas acquisition device 1. Further, the percentage of the condensate obtained by condensation in the first reactor 2 to the total condensate supplied to the purification device 5 is reduced to 80.6%. The remaining condensate is the condensate obtained by condensation in the condensing device 7.

Comparative Example

Figure 8:
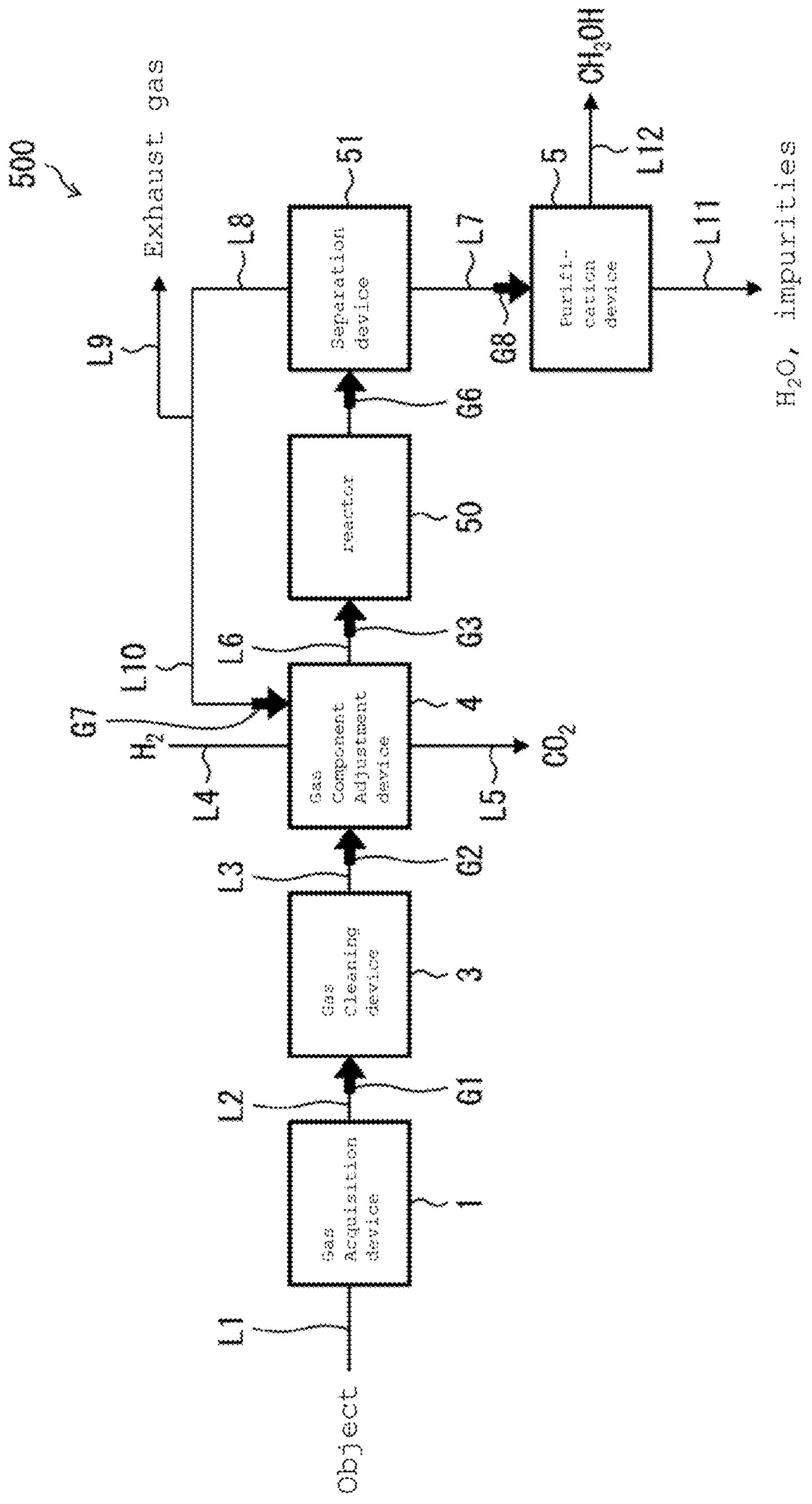
FIG. 8 is a system diagram schematically illustrating a configuration of a methanol production apparatus according to a comparative example of the present invention.

In the present comparative example, a specific example of a method for producing methanol that is outside the scope of the present invention will be described. FIG. 8 is a system diagram schematically illustrating a configuration of a production apparatus 500 according to the comparative example. In the comparative example, a method for producing methanol performed using the production apparatus 500 illustrated in FIG. 8 will be described.

The production apparatus 500 is different from the production apparatus 100 of Example 1 in that the production apparatus 500 includes a reactor 50 outside the scope of the present invention and a separation device 51 instead of the first reactor 2 within the scope of the present invention. More specifically, the reactor 50 is a reactor that performs a conversion reaction of methanol, but is not an internal condensation reactor that condenses a high-boiling-point component containing methanol obtained as a result of the conversion and water and discharges the condensed product to the outside of the reaction system. Other configurations are the same as those of the production apparatus 100 of Example 1.

In the production apparatus 500, a waste material as an object is supplied to a gas acquisition device 1 via a path L1, and a waste material-derived gas G1 is obtained. The composition of the waste material-derived gas G1 obtained in the gas acquisition step S1 is 45 vol % of $H_2$, 30 vol % of CO, 20 vol % of $CO_2$, and 5 vol % of $N_2$.

The obtained waste material-derived gas G1 is supplied to a gas cleaning device 3 via a path L2, and a cleaned gas G2 is obtained.

The obtained cleaned gas G2 is supplied to a gas component adjustment device 4 via a path L3. In addition, the unreacted gas circulated from the downstream separation device 51 is supplied to the gas component adjustment device 4 via a path L10. The index SN of an adjusted gas G3 discharged from the gas component adjustment device 4 is adjusted to 2 by the addition of $H_2$ via a path L4.

The adjusted gas G3 having the adjusted index SN is supplied to the reactor 50 via a path L6 and converted into methanol and water.

The produced methanol and water are supplied to the separation device 51 as a gas mixture G6 together with the unreacted gas. In the separation device 51, the gas mixture G6 is separated into an unreacted gas G7 and a condensate G8 by a gas-liquid separation operation.

The unreacted gas is discharged from the separation device 51 via a path L8. Of the discharged unreacted gas, 50% is returned to the gas component adjustment device 4 via the path L10 and reused, and the remaining 50'% is discharged as exhaust gas via a path L9.

The condensate G8 obtained from the separation device 51 is supplied to the purification device 5 via a path L7. Water and impurities removed from the supplied condensate are discharged via a path L11, and purified methanol is obtained via a path L12.

According to the present comparative example, methanol can be synthesized by acquiring the waste material-derived gas G1 from the waste material, and using the gas as a source gas. Further, according to the present comparative example, methanol is obtained at a yield of 56.0% based on carbon atoms of the carbon oxide contained in the waste material-derived gas G1 obtained in the gas acquisition device 1.

Summary of Examples

From the above results, the percentage of the obtained methanol based on carbon atoms of the carbon oxide contained in the waste material-derived gas G1 obtained in the gas acquisition device 1 is 56.0% in the comparative example outside the scope of the present invention, whereas the percentage is 88.3% in Examples 1 and 2 within the scope of the present invention. From this, it was demonstrated that according to the present invention, the percentage of the obtained methanol based on carbon atoms of the carbon oxide contained in the waste material-derived gas G1 obtained in the gas acquisition device 1 is greatly improved. This means that according to the present invention, the yield of methanol based on carbon atoms of the carbon oxide contained in the waste material-derived gas G1 supplied as a source gas is improved. That is, it was demonstrated that according to the present invention, methanol can be efficiently produced by using a waste material-derived gas acquired from a waste material as a source gas.

In Example 3, the percentage of the obtained methanol based on carbon atoms of the carbon oxide contained in the waste material-derived gas G1 obtained in the gas acquisition device 1 is 91.5%. From this, it was demonstrated that addition of the preliminary conversion step and the condensation step further improves the percentage of the obtained methanol based on carbon atoms of the carbon oxide contained in the waste material-derived gas G1 obtained in the gas acquisition device 1.

Further, in Example 3, the percentage of the condensate obtained by condensation in the first reactor 2 to the condensation amount of the total condensate is reduced to 80.6%. From this, it was demonstrated that addition of the preliminary conversion step and the condensation step reduces the percentage of the condensate obtained by condensation in the first reactor 2 to the condensation amount of the total condensate.

DESCRIPTION OF REFERENCE SIGNS

S1 Gas acquisition step
S2 Gas cleaning step
S3 Gas adjustment step
S4 Preliminary conversion step

S5 Condensation step
S6 Conversion step
S7 Purification step
1 Gas acquisition device
2 First reactor
3 Gas cleaning device
4 Gas component adjustment device
5 Purification device
6 Second reactor
7 Condensing device FIG. 1
S1 Gas acquisition step
S2 Gas cleaning step
S3 Gas adjustment step
S6 Conversion step
S7 Purification step FIG. 2
(1) Object
(2) Exhaust gas
(3) $H_2O$, impurities
1 Gas acquisition device
2 First reactor
3 Gas cleaning device
4 Gas component adjustment device
5 Purification device FIG. 3
(1) Source gas
(2) Condensate FIG. 4
S1 Gas acquisition step
S2 Gas cleaning step
S3 Gas adjustment step
S4 Preliminary conversion step
S6 Conversion step
S7 Purification step FIG. 5
(1) Object
(2) Exhaust gas
(3) $H_2O$, impurities
1 Gas acquisition device
2 First reactor
3 Gas cleaning device
4 Gas component adjustment device
5 Purification device
6 Second reactor FIG. 6
S1 Gas acquisition step
S2 Gas cleaning step
S3 Gas adjustment step
S4 Preliminary conversion step
S5 Condensation step
S6 Conversion step
S7 Purification step FIG. 7
(1) Object
(2) Exhaust gas
(3) $H_2O$, impurities
1 Gas acquisition device
2 First reactor
3 Gas cleaning device
4 Gas component adjustment device
5 Purification device
6 Second reactor
7 Condensing device FIG. 8
(1) Object
(2) Exhaust gas
(3) $H_2O$, impurities
1 Gas acquisition device
3 Gas cleaning device
4 Gas component adjustment device
5 Purification device
50 Reactor
51 Separation device

The invention claimed is:

1. A method for producing methanol, the method comprising:

a gas acquisition step of obtaining a gas containing a carbon oxide and hydrogen from a waste material; and a conversion step of bringing at least a portion of the gas into contact with a catalyst to convert the portion of the gas into methanol in a gas phase, the method further comprising, between the gas acquisition step and the conversion step, a preliminary conversion step of converting the carbon oxide and hydrogen in the gas until a conversion rate reaches a predetermined equilibrium conversion rate or more, wherein the conversion step is performed in a first reactor, which includes a reaction vessel having a condensing surface to condense a high-boiling-point component containing methanol and water, in the conversion step, a reaction is allowed to proceed by condensing a high-boiling-point component containing methanol obtained as a result of the conversion and water at the condensing surface and then discharging a condensed product to an outside of a reaction system, and the preliminary conversion step is performed in a second reactor, which includes a general fixed bed catalyst reactor filled with a solid catalyst.

2. The method for producing methanol according to claim 1, wherein the predetermined equilibrium conversion rate is 80% of an equilibrium conversion rate of the carbon oxide in the gas based on carbon.

3. The method for producing methanol according to claim 2, further comprising, between the preliminary conversion step and the conversion step, a condensation step of condensing a reaction gas generated in a preliminary conversion reaction in the preliminary conversion step and discharging a high-boiling-point component in the reaction gas to the outside of the reaction system.

4. The method for producing methanol according to claim 1, wherein in the conversion step, a conversion rate into methanol of at least one of the carbon oxide and hydrogen in the gas to be subjected to the conversion step is 60% or more.

5. The method for producing methanol according to claim 1, further comprising, between the gas acquisition step and the conversion step, a gas adjustment step of adjusting a component of the gas to be subjected to the conversion step.

6. The method for producing methanol according to claim 2, further comprising, between the gas acquisition step and the preliminary conversion step, a gas adjustment step of adjusting a component of the gas to be subjected to the preliminary conversion step.

7. The method for producing methanol according to claim 5, wherein the gas adjustment step includes:

removing at least a portion of carbon dioxide from the gas; or adding hydrogen gas to the gas.

8. The method for producing methanol according to claim 5, wherein the gas adjustment step is performed by removing at least a portion of carbon dioxide from the gas using a separation membrane that is selectively permeable to carbon dioxide or a separation membrane that selectively inhibits permeation of carbon dioxide.

9. The method for producing methanol according to claim 5, wherein the gas adjustment step is performed by decomposing or reforming at least a portion of the carbon oxide in the gas.

10. The method for producing methanol according to claim 5, wherein the gas adjustment step is performed by adding hydrogen to the gas.

11. The method for producing methanol according to claim 1, wherein the gas to be subjected to the conversion step has a value of an index SN calculated by Formula (I) shown below of 1 or more and 10 or less:

$$SN=(yH_2-yCO_2)/(yCO+yCO_2) \quad (I)$$

wherein $yH_2$, $yCO_2$, and yCO are respectively volume fractions of hydrogen, carbon dioxide, and carbon monoxide in the gas to be subjected to the conversion step.

12. The method for producing methanol according to claim 5, wherein the gas adjustment step is performed by at least one of:

(i) adding hydrogen to the gas;

(ii) removing at least a portion of carbon dioxide from the gas; and (iii) decomposing or reforming at least a portion of the carbon oxide in the gas.

* * * * *